United States Patent [19]

Drake

[11] 4,417,089

[45] Nov. 22, 1983

[54] HYDROISOMERIZATION

[75] Inventor: Charles A. Drake, Bartlesville, Okla.

[73] Assignee: Phillips Petroleum Company, Bartlesville, Okla.

[21] Appl. No.: 413,646

[22] Filed: Sep. 1, 1982

[51] Int. Cl.³ .............................................. C07C 5/25
[52] U.S. Cl. .................................... 585/670; 208/138; 252/462; 502/314; 502/323
[58] Field of Search ................. 585/670, 669; 208/138

[56] References Cited

U.S. PATENT DOCUMENTS

| | | | |
|---|---|---|---|
| 2,952,719 | 9/1960 | Appell | 260/683.2 |
| 3,078,323 | 2/1963 | Kline et al. | 260/683.65 |
| 3,223,617 | 12/1965 | Maziuk | 208/138 |
| 3,247,099 | 4/1966 | Oleck | 208/138 |
| 3,268,617 | 8/1966 | Menapace et al. | 260/683.2 |
| 3,409,699 | 11/1968 | Mitsche | 585/670 |
| 3,409,699 | 11/1968 | Mitsche | 260/683.2 |
| 3,412,163 | 11/1968 | De Rosset | 260/666 |
| 3,428,704 | 2/1969 | Fishel | 260/683.2 |
| 3,436,335 | 4/1969 | Maziuk | 208/138 |
| 3,437,698 | 4/1969 | O'Grady et al. | 260/615 |
| 3,467,728 | 9/1969 | Hervert | 260/683.2 |
| 3,531,545 | 9/1970 | Garner et al. | 260/683.2 |
| 3,541,001 | 11/1970 | Hirschler | 208/138 |
| 3,661,738 | 5/1972 | Davis, Jr. et al. | 208/138 |
| 3,679,773 | 7/1972 | Kovach et al. | 260/683.3 |
| 3,700,745 | 10/1972 | Kovach et al. | 260/672 R |
| 3,792,109 | 2/1974 | Trepka et al. | 260/683.2 |
| 3,793,257 | 2/1974 | Pennella et al. | 260/683.2 |
| 3,867,305 | 2/1975 | Flanigen et al. | 585/670 |
| 3,894,110 | 7/1975 | Drehman | 260/680 R |
| 3,903,020 | 9/1975 | Sergeys et al. | 252/455 R |
| 3,903,190 | 9/1975 | Pennella | 260/683.2 |
| 3,917,739 | 11/1975 | Parthasarathy et al. | 260/683.65 |
| 4,006,074 | 2/1977 | Erickson | 208/138 |
| 4,024,077 | 5/1977 | Engelhard et al. | 252/442 |
| 4,082,815 | 4/1978 | Johnson et al. | 260/683.2 |
| 4,087,472 | 5/1978 | Hughes | 568/906 |
| 4,131,630 | 12/1978 | Hughes | 260/666 |
| 4,152,351 | 5/1979 | Drake | 260/465.8 R |
| 4,227,993 | 10/1980 | Engelhard et al. | 585/669 |
| 4,293,728 | 10/1981 | Montgomery | 585/670 |

FOREIGN PATENT DOCUMENTS

| | | | |
|---|---|---|---|
| 1386551 | 12/1964 | France | 208/138 |
| 966062 | 8/1964 | United Kingdom | 585/670 |

*Primary Examiner*—Delbert E. Gantz
*Assistant Examiner*—Cynthia A. Prezlock

[57] ABSTRACT

The hydroisomerization of terminal olefins to internal olefins can be effectively carried out using a catalyst which consists essentially of a palladium component, a cerium component, and alumina.

6 Claims, No Drawings

HYDROISOMERIZATION

BACKGROUND

The double bond isomerization of olefin-containing compounds in the presence of hydrogen is known as hydroisomerization. The catalytic hydroisomerization of terminal olefins, i.e., 1- or alpha-olefins to internal olefins, e.g., 2- or beta-olefins, can be effectively carried out using various metal-containing catalysts.

INVENTION

It has been discovered that the hydroisomerization of terminal olefins to internal olefins can be carried out using supported catalysts which contain cerium, palladium, and alumina components.

In one embodiment, 1-olefins are converted to an approximately equal mixture of cis- and trans-2-olefins in the presence of hydrogen using a palladium/cerium on alumina catalyst. Thus, 1-pentene is converted to a 50:50 mixture of cis- and trans-2-pentenes with 96.6% conversion and 91.2% selectivity in about 10 minutes at 130° C. over Pd/Ce on alumina catalyst.

OBJECTS OF THE INVENTION

It is an object of the invention to provide a process for the catalytic conversion of terminal olefins to internal olefins in the presence of hydrogen.

It is another object of the invention to provide a process for the hydroisomerization of 1-olefins to 2-olefins using a specified catalyst.

It is another object of the invention to provide a process for the hydroisomerization of certain 1-olefins to 2-olefins.

ADVANTAGES

The process of the invention has several advantages over other processes of converting 1-olefins to 2-olefins. The cis/trans product isomer ratios obtained using the process of the invention are generally about 50/50. The conversions take place in relatively short periods of time, i.e., about 4-10 minutes.

Applicant's reaction conditions, i.e., temperature and pressure, are mild when compared to prior art isomerization conditions. In addition, the preparation of applicant's catalysts is relatively simple and straight-forward.

Other aspects and advantages of the invention will become apparent from the reading of the applicant's specification and claims.

DESCRIPTION OF THE INVENTION

The hydroisomerizations carried out in accordance with the invention involve the use of catalysts contaning (A) a palladium component, (B) a cerium component, and (C) an alumina support. Other conventional ingredients can also be present.

The Palladium Component

The palladium component of the inventive catalyst can be in the form of finely divided palladium metal or compouns of palladium which are reducible by hydrogen to palladium metal. The palladium component is preferably used in the form of palladium metal deposited on a suitable support or in the form of hydrogen-reducible compounds of palladium on a suitable support.

Compounds of palladium which are reducible by hydrogen to palladium metal include the oxides, halides, nitrates, sulfates, oxalates, acetates, carbamates, propionates, tartrates, hydroxides, and the like, and mixtures thereof. Exemplary compounds include palladium oxide, palladium chloride, palladium nitrate, palladium acetate, palladium carbonate, palladium hydroxide, palladium oxalate, and the like.

The Cerium Component

The cerium component of the catalyst can be finely divided elemental cerium, or compouns of cerium reducible to finely divided cerium by hydrogen. Preferably, the cerium component will comprise cerium or a cerium compound reducible by hydrogen to cerium metal when deposited on a suitable support.

The compounds of cerium which are reducible by hydrogen to elemental cerium include oxides, halides, nitrates, hydroxides, acetates, oxalates, carbonates, propionates, tartrates, and the like, and mixtures thereof. Specific examples of useful cerium compounds include cerium (III) oxide, cerium (IV) oxide, cerium triacetate, cerium trichloride, cerium trihydroxide, cerium nitrate, and the like.

The weight ratio of palladium to cerium in the mixed catalyst of the invention will generally lie within the range of about 0.1:1 to about 10:1, preferably within the range of about 0.3:1 to about 3:1.

The Alumina Component

Generally, the alumina component employed will be a high surface area alumina. Gamma-, eta-, and beta-aluminas are operable. "High surface area" generally means a surface area of about 25–700 m$^2$/g, with surface areas of 100–300 m$^2$/g preferred. Alumina-containing materials, such as combinations containing alumina and other refractory oxides or other conventional carrier components, can be used. While combinations containing at least one of silica, magnesia, thoria, zirconia, and the like, are operable, it is generally preferred to use a high surface area alumina alone.

The amount of alumina or alumina-containing material employed in the catalyst of the invention may vary. Generally, those amounts which assure a high rate of hydroisomerization activity will be employed. Typical catalysts used in accordance herewith will contain about 0.1 to about 10.0, and preferably about 0.25 to about 5.0, weight percent of palladium and cerium combinations, with the balance being alumina or alumina-containing material.

Other modifiers may be present either as catalyst components or as additives to the feedstream. When present, they will be used in quantities consistent with their functions.

Preparation of the Catalyst

The catalysts used herein are generally prepared by contacting the palladium and cerium components, either at the same time or in any suitable order, with a support component. A typical catalyst preparation can be described as follows:

The mixture of palladium and cerium can be prepared in any convenient manner. For example, a mixture of palladium or a reducible compound of palladium and cerium or a reducible cerium compound can be codeposited from a solution onto a support. The palladium or reducible compound of palladium and cerium or reducible compound of cerium can also be deposited on the support separately or in any order. Suitable solvents include those in which the palladium or reducible compound of palladium and cerium or reducible compound of cerium are soluble such as alcohols, nitriles, organic and inorganic acids, water, and the like, and mixtures thereof. Exemplary solvents include acetonitrile, acetic acid, aqueous hydrochloric acid, methanol, ethanol, and water.

Typically, the minimum volume of solvent necessary to suspend or dissolve the palladium or reducible compound of palladium and the cerium or reducible compound of cerium is employed. The support is soaked in the palladium/cerium containing solution for sufficient time to allow adsorption of the metal components dissolved therein. Typically, 15 minutes to 2 hours are suitable. Excess solvent is then removed, for example, by drying the wet catalyst on the rotary evaporator. The dired catalyst is calcined in air at temperatures of 300°–700° C. for about ½ hour to about 4 hours, and then reduced under hydrogen atmosphere at temperatures of 300°–700° C. for about ½ hour to about 4 hours.

The Organic Feed

The organic feeds to be hydroisomerized, i.e., converted to internal olefins, in accordance with the invention include unsaturated compounds of the general formula $$H_2C=CR'-R''$$

wherein R' is methyl or hydrogen, with hydrogen preferred, and R" is an organic moiety containing from 2 to 30 carbon atoms.

Useful compounds include terminally unsaturated olefins containing from about 4 to about 33 carbon atoms, with those containing 4 to 10 carbon atoms preferred. Typical 1-olefins to be employed as an organic feed include: 1-butene, 1-pentene, 4-methyl-1-pentene, 1-hexene, 3-ethyl-1-hexene, 5-ethyl-1-octene, 1-decene, and the like, and mixtures thereof. Preferred are straight chain 1-olefins with 5–10 carbons. Especially preferred is 1-pentene.

Hydroisomerization Conditions

Generally, a conversion of terminal olefins to internal olefins in accordance with the invention will take place in the liquid or gas phase, depending upon the character of the feed and the type of apparatus employed. A typical conversion reaction will involve the gas phase conversion of 1-olefins to 2-olefins in a tubular reactor. Suitable reaction devices include a stirred tank reactor or the like.

Conversion temperatures will usually lie between about 80° and about 250° C., with about 130–170° C. preferred. At these temperatures, the production of a 50:50 cis/trans isomer mixture is optimized.

Hydrogen is required in the practice of the invention. The order of addition is unimportant, i.e., the hydrogen can be introduced prior to, concurrent with, or subsequent to the time that hydrocarbon is brought in contact with the catalyst. For example, the hydrogen and hydrocarbon stream may be admixed prior to contacting the catalyst. The hydrocarbon, the hydrogen, or both, can be added undiluted, or diluted with a suitable inert medium such as inert gases and saturated hydrocarbons. Exemplary inert gases include nitrogen, argon, carbon dioxide, and the like. Exemplary saturated hydrocarbons include methane, ethane, propane, butane, isobutane, pentane and the like, and mixtures thereof.

The hydrogen is added at the rate of about 10 to about 1000 LHSV, with about 100 LHSV preferred.

The invention can be carried out under varying pressure conditions. Pressures employed are generally about 100 mm Hg to about 120 psig, preferably from about 1 atm. to about 70 psig most preferably about 30 psig. Space velocities of about 0.2 to about 10, preferably about 0.5 to 5 LHSV are operable.

Product Recovery

Suitable techniques for recovery of the internal olefins produced in accordance with the invention include distillation, selective adsorption, and the like. Other conventional recovery techniques, as well as other processes, not associated with the handling and storage of internal olefins may be used in conjunction with the process of the invention.

EXAMPLE I

Catalyst Preparation

Control catalysts A-E were obtained from commercial sources, as indicated in Table I.

Invention catalyst F was prepared as follows. A solution containing 0.5 g Pd(OAc)$_2$ and 0.6 g Ce(OAc)$_3$ in about 50 mL of glacial acetic acid was added to a beaker containing 50 g of T1370 (alumina support from Catalysts and Chemicals, Inc., Louisville, Ky). The mixture was allowed to stand for 30–60 minutes, the solvent was removed on the rotary evaporator. Dried catalyst was calcined in air at 350° C. for about 3 hours, followed by hydrogen reduction at 350° C. for about 3 hours.

TABLE I

| CATALYST | Support | Metal Loading | Supplier (Catalyst number) |
|---|---|---|---|
| A | Al$_2$O$_3$ | 0.5% Pd | Engelhard Industries (#25359) |
| B | Al$_2$O$_3$ | 0.5% Pd | Catalysts and Chemicals, Inc. (#T-1370 Pd) |
| C | Al$_2$O$_3$ | Pd | Harshaw Chemical Co. (#Pd-0803) |
| D | Al$_2$O$_3$ | 0.3% Pt | Calsicat Div., Mallinchrodt, Inc. (#05B-027D) |
| E | Catapol SB | 0.5% Pd | Catalysts and Chemicals, Inc. (#L-119) |
| F | Al$_2$O$_3$ | 0.5% Pd + 0.5% Ce | Invention catalyst |

EXAMPLE II

Control catalysts A-E were subjected to a variety of hydroisomerization conditions, as summarized in Table II. Variable 1-pentene feed rate, reaction pressures, hydrogen/diluent ratios and reaction temperatures were studied.

TABLE II

| Run # | Catalyst | 1-Pentene feed rate, mL/hr | Gas Flow mL/min H$_2$ | Gas Flow mL/min N$_2$ | Reaction Conditions Temp., °C. | Reaction Conditions Press., psig | 1-Pentene Conversion, % | 2-Pentene Selectivity, % |
|---|---|---|---|---|---|---|---|---|
| 1 | A | 36 | 20 | 60 | 25 | 30 | 53.8 | 8.5 |
| 2 |   | 36 | 40 | 60 | 25 | 30 | 43.6 | 41.5 |

TABLE II-continued

| Run # | Catalyst | 1-Pentene feed rate, mL/hr | Gas Flow mL/min H₂ | N₂ | Reaction Conditions Temp., °C | Press., psig | 1-Pentene Conversion, % | 2-Pentene Selectivity, % |
| --- | --- | --- | --- | --- | --- | --- | --- | --- |
| 3 |   | 36 | 60 | 60 | 25  | 30 | 50.5 | 41.8 |
| 4 | B | 36 | 20 | 60 | 90  | 30 | 62.8 | 86.3 |
| 5 |   | 36 | 20 | 60 | 110 | 30 | 69.4 | 82.4 |
| 6 |   | 36 | 40 | 60 | 110 | 30 | 79.3 | 79.4 |
| 7 |   | 36 | 60 | 60 | 110 | 30 | 84.7 | 75.9 |
| 8 |   | 36 | 60 | 60 | 130 | 30 | 92.8 | 71.3 |
| 9 |   | 36 | 40 | 60 | 130 | 30 | 89.6 | 82.6 |
| 10 |   | 36 | 40 | 60 | 150 | 30 | 91.4 | 83.2 |
| 11 |   | 36 | 20 | 60 | 150 | 30 | 81.1 | 85.9 |
| 12 |   | 36 | 0  | 60 | 150 | 30 | 39.1 | 06.9 |
| 13 |   | 36 | 0  | 60 | 170 | 30 | 44.5 | 96.9 |
| 14 |   | 36 | 20 | 60 | 170 | 30 | 85.7 | 89.1 |
| 15 |   | 36 | 0  | 60 | 200 | 30 | 55.5 | 97.8 |
| 16 |   | 36 | 20 | 60 | 200 | 30 | 80.6 | 79.7 |
| 17 |   | 36 | 40 | 60 | 200 | 30 | 84.8 | 73.9 |
| 18 | C | 72 | 20 | 60 | 130 | 70 | 23.3 | 61.4 |
| 19 | D | 72 | 20 | 60 | 130 | 70 | 23.3 | 55.4 |
| 20 | E | 72 | 20 | 60 | 130 | 70 | 49.4 | 91.5 |
| 21 |   | 72 | 20 | 60 | 150 | 70 | 52.8 | 81.1 |

This example demonstrates that palladium on alumina catalyst promotes the isomerization of 1-pentene to 2-pentene. Note, however, that high conversions (>80%) are typically accompanied by low selectivity to the desired 2-pentene. High selectivities (>90%) to the desired product, 2-pentene, are only obtained where low conversions (>60%) per pass are observed.

EXAMPLE III

Invention catalyst F was subjected to a variety of hydroisomerization conditions, as summarized in Table III. Variable 1-pentene feed rate, reaction pressures, hydrogen/diluent ratios and reaction temperatures were studied.

TABLE III

| Run # | 1-Pentene feed rate, mL/hr | mL/min H₂ | N₂ | Reaction Conditions Temp., °C | Press., psig | 1-Pentene Conversion, % | 2-Pentene Selectivity, % |
| --- | --- | --- | --- | --- | --- | --- | --- |
| 1  | 36 | 20 | 60  | 170 | 30 | 94.0 | 88.9 |
| 2  | 36 | 20 | 60  | 200 | 30 | 96.5 | 65.8 |
| 3  | 36 | 20 | 120 | 170 | 30 | 89.8 | 86.3 |
| 4  | 72 | 20 | 60  | 170 | 30 | 94.8 | 73.9 |
| 5  | 72 | 40 | 60  | 170 | 30 | 92.2 | 78.6 |
| 6  | 72 | 40 | 120 | 170 | 30 | 87.5 | 91.9 |
| 7  | 72 | 40 | 120 | 130 | 30 | 91.6 | 90.5 |
| 8  | 72 | 40 | 120 | 120 | 30 | 90.3 | 90.8 |
| 9  | 72 | 40 | 120 | 110 | 30 | 89.0 | 90.7 |
| 10 | 72 | 40 | 120 | 130 | 30 | 91.6 | 90.5 |
| 11 | 72 | 40 | 120 | 130 | 50 | 95.6 | 84.6 |
| 12 | 72 | 40 | 120 | 130 | 10 | 86.5 | 95.8 |
| 13 | 72 | 40 | 120 | 130 | 0  | 77.4 | 97.8 |
| 14 | 72 | 40 | 120 | 110 | 70 | 91.5 | 83.7 |
| 15 | 72 | 40 | 120 | 150 | 70 | 95.9 | 84.8 |
| 16 | 72 | 40 | 120 | 130 | 50 | 95.2 | 88.8 |
| 17 | 72 | 40 | 120 | 130 | 70 | 96.1 | 85.1 |
| 18 | 72 | 60 | 120 | 130 | 70 | 96.9 | 76.8 |
| 19 | 72 | 20 | 120 | 130 | 90 | 96.6 | 91.2 |
| 20 | 72 | 40 | 120 | 130 | 90 | 97.3 | 79.2 |
| 21 | 72 | 40 | 180 | 130 | 90 | 97.3 | 75.6 |
| 22 | 72 | 20 | 180 | 130 | 90 | 97.1 | 84.6 |

This example demonstrates the effectiveness of the inventive hydroisomerization process for the conversion of 1-pentene to 2-pentene. Excellent conversions (>80%) and selectivities (>80%) are obtained in most cases under a variety of reaction conditions. Under optimum conditions, as illustrated by runs 7, 8, 10, and 19, 1-pentene conversions in excess of 90% with greater than 90% selectivity to the desired product, 2-pentene, are achieved.

Reasonable variations, such as those which would occur to one of ordinary skill in the art, may be made herein without departing from the scope of the invention.

I claim:

1. A process for converting terminal olefins to internal olefins comprising contacting at least one terminal olefin reactant with a catalyst in the presence of hydrogen wherein the catalyst consists essentially of
   (a) a palladium component,
   (b) a cerium component, and
   (c) alumina.

2. The process of claim 1 wherein the palladium and cerium components are present in ratios of about 0.1:1 to about 10:1.

3. The process of claim 2 wherein the palladium and cerium components are present in ratios of about 1:3 to about 3:1.

4. The process of claim 3 wherein the catalyst contains about 0.5 weight percent cerium, about 0.5 weight percent palladium, and the balance alumina.

5. A process of claim 4 wherein the terminal olefin employed is a compound of the general formula $$H_2C=CR'-R''$$

wherein R' is methyl or hydrogen, and R'' is an organic moiety containing from about 2 to 30 carbon atoms.

6. A process of claim 4 wherein the terminal olefin is 1-pentene.